United States Patent [19]

Bailey

[11] Plant 4,011

[45] Jan. 25, 1977

[54] ROSE PLANT

[75] Inventor: Dorothy Jean Searles Bailey, Bakersfield, Calif.

[73] Assignee: San Joaquin Rose Co., McFarland, Calif.

[21] Appl. No.: 661,276

[22] Filed: Feb. 25, 1976

[51] Int. Cl.[2] ..... A01H 5/00

[52] U.S. Cl. ..... Plt./3

[58] Field of Search ..... Plt./3

*Primary Examiner*—Robert E. Bagwill
*Attorney, Agent, or Firm*—Vincent G. Gioia

CLAIM

A new and distinct variety of rose plant of the climber class, substantially as shown and described, characterized particularly by recurrent flowers of yellow coloring starting as buds of yellow-yellow orange tonality maturing to flowers of strong yellow coloring and good petalage, borne singly and in small clusters with little color change as the flowers age, on a vigorous plant having dark green, thick, holly-like foliage resistant to blackspot and mildew and very winter-hardy.

1 Drawing Figure

1

The present invention relates to a new and distinct variety of rose plant of the climber class, which was originated by my crossing as seed parent the rose variety known as "Golden Showers" with the rose variety known as "Gold Rush" as pollen parent.

Among the novel characteristics possessed by this new variety which distinguish it from its parents and all other varieties of which I am aware are:

1. recurrent flowers of strong yellow coloring giving a pleasing, rich tannish yellow tonality from a distance,
2. stable bloom coloring, without streaking, that holds until petals fall and
3. a vigorous plant which is very "winter hardy."

Asexual reproduction by budding of the new variety as performed in Kern County, California, shows that the foregoing and other distinguishing characteristics come true to form and are established and transmitted through succeeding propagations.

The new and improved rose variety which I have developed is an unusually fine yellow climber exhibiting vigorous growth typical of climbing varieties and unusually stable yellow coloring and recurrent flowering habit. The yellow toned blooms are of relatively high petalage, i.e., 38 to 42 petals, under normal conditions and differ significantly from its seed parent "Golden Showers" in this respect. Blooms are also unusually large, i.e., 5 to 5½ inches, and are borne generally singly on long stems but sometimes with side buds. The yellow-yellow orange buds open into bright flowers which remain stable on maturity and exhibit no streaking. The general tonality of this new variety exhibits a pleasing tannish-yellow affect from a distance. The flowers themselves are long lasting on the plant and after cutting are not easily marred by sun or light rain. This upright growing variety is capable of obtaining a height of 6 to 8 feet during the first growing season. The plant exhibits an unusual degree of winter hardiness for a yellow rose and climber of this nature.

The accompanying drawing shows typical specimens of the vegetative growth and flowers of the new variety in different stages of development and as depicted in color as nearly true as it is reasonably possible to make the same in a color illustration of this character.

2

The following is a detailed description of my new variety, with color terminology in accordance with the Royal Horticultural Society Color Chart (RHSCC). The terminology used in color description herein refers to plate numbers in the aforementioned color chart, e.g., "45B" is plate 45B of the Royal Horticultural Society Color Chart.

Parentage: Seedling.
*Seed parent.*—"Golden Showers".
*Pollen parent.*—"Gold Rush".
Class: Climber.

The following observations are made of specimens grown outdoors at Kern County, Calif., during the month of June.

FLOWER

Blooming Habit: Recurrent.
Bud:
*Size.*—Large.
*Form.*—Long pointed.
*Color.*—When sepals first divide — yellow orange between 22A and 19A. When petals begin to unfurl — yellow orange near 16A. When half-blown: inside of petals — near 15D with edge highlighted with 13D; reverse side of petals — near 13C.
*Sepals.*—Spear shaped with narrow claw point; short for size and length of bud, recurls freely.
*Peduncle.*—Length — short; Aspect — stiff with foliage appearing 3 to 4 inches from base of bud; Strength — strong, erect; Color — near 136A green, slight mottling at base of bud.
Bloom:
*Size.*—Average size when fully expanded — 5 to 5½ inches.
*Borne.*—Generally single on long stem with some side buds.
*Form.*—High centered at first; becoming flat; petals remaining at first loosely rolled outward; petals recurl with point at tip, center loose with peaked cup.
*Petalage.*—Number of petals under normal conditions — 38 to 42 with 10 to 12 small petaloids.

*Color.*—(during first 2 days); Inner petals at center of flower — yellow orange near 16A; Outer petals — 13C; Base of petals (point of attachment) — near 19A; Reverse of petals — near 22A; General tonality from a distance — pleasing rich tannish yellow between 15D and 13D with no streaking or blotching.

*Color Change.*—as bloom ages — Little change; General tonality — holds stable color until petals drop clean.

Petals:

*Texture.*—Thick, lots of substance.

*Appearance.*—Petals have soft, satiny sheen on upper surface.

*Form.*—Rounded at base and tapered at apex with one, and on occasion, two small uniform notches at point of recurl.

*Arrangement.*—Imbricated having usually 6 petals to a row.

*Petaloids in center.*—10 to 12 in varying sizes.

*Persistence.*—Drop off cleanly.

*Fragrance.*—Light, fruity.

*Lasting Quality.*—Long lasting on plant and as cut; petals not marred by sun, dew, or light rain.

REPRODUCTIVE ORGANS

Stamens, filaments and anthers:

*Arrangement.*—Regularly arranged around styles.

*Color.*—Yellow — 13B.

Pollen: Color — yellow orange 22A.

Styles: Bunches, quite uniform in length, strong and thick.

Stigmas: Color — yellow 4C.

Hips: Shape — Globular becoming pear shaped at peduncle; Size — Large; Color — orange 25B when mature; Do seeds protrude: Seldom, usually contained in side hip.

PLANT

Form: Upright.

Growth: Very vigorous grower; Height attained — 6 to 8 feet first season.

Foliage: Compound of 5 to 7 leaflets.

*Size.*—Large.

*Quantity.*—Abundant.

*Color.*—New foliage: Upper side — medium green 137B with veining and some blotching of red 58A; Under side — 37D with 58A. Old foliage: Upper side — 133A; Under side — 138B.

*Shape.*—Oval at base, longer than average and pointed.

*Texture.*—Upper side — waxed and thick, holly-like; Underside — rough and ridged.

*Edge.*—Mostly smooth with slight serration toward tip.

*Serration.*—Small and single.

*Leaf Stem.*—Color — Green 141D; Under side — near 141D, smooth.

*Stipules.*—Medium length bearded.

*Resistance to Disease.*—Blackspot — above average; Mildew — above average; Rust — none observed.

Wood:

*New Wood.*—Color — yellow-green 146A; Bark: Smooth.

*Old Wood.*—Color — Green, almost identical to foliage 133A; Bark — Smooth.

Thorns:

*Thorns.*—Quantity: on main stalks from base — ordinary; On laterals from stalk — few; Form — flat base slight downward curve; Length — Large; Color (when young) — grayed red 182A; Position — irregular.

*Prickles.*—Quantity: on main stalks — normal; On laterals — A few small prickles on peduncle.

Winter Hardiness: Very winter hardy.

I claim:

1. A new and distinct variety of rose plant of the climber class, substantially as shown and described, characterized particularly by recurrent flowers of yellow coloring starting as buds of yellow-yellow orange tonality maturing to flowers of strong yellow coloring and good petalage, borne singly and in small clusters with little color change as the flowers age, on a vigorous plant having dark green, thick, holly-like foliage resistant to blackspot and mildew and very winter-hardy.

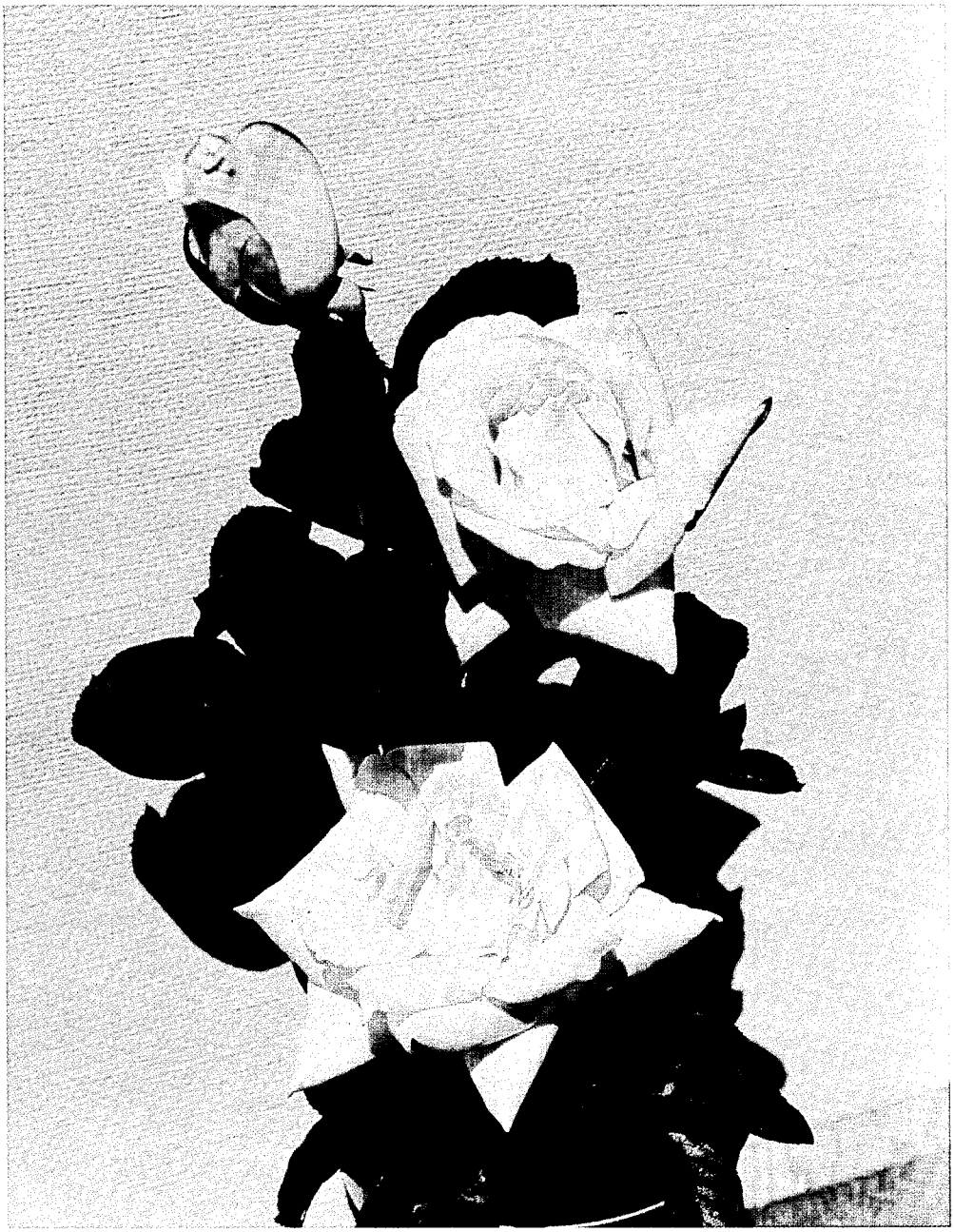

* * * * *